United States Patent [19]

Fortier et al.

[11] Patent Number: 4,970,170
[45] Date of Patent: Nov. 13, 1990

[54] LIQUID CHROMATOGRAPHIC DETERMINATION OF WATER

[75] Inventors: Nancy E. Fortier, Fairfield, Ohio; James S. Fritz, Ames, Iowa

[73] Assignee: Iowa State University Research Foundation, Inc., Ames, Iowa

[21] Appl. No.: 220,743

[22] Filed: Jul. 18, 1988

[51] Int. Cl.$^5$ .................... G01N 21/75; G01N 30/74; G01N 33/18
[52] U.S. Cl. ........................................ 436/39; 436/40; 436/140; 436/161; 436/164; 436/166; 210/656
[58] Field of Search .................... 436/39-42, 436/177, 161, 164, 166, 140; 210/656, 662, 689; 73/61.1 C, 61.1 R; 356/436

[56] References Cited

U.S. PATENT DOCUMENTS

| | | | |
|---|---|---|---|
| 2,844,025 | 7/1958 | Joyce et al. | 436/39 |
| 3,118,735 | 1/1964 | Favre et al. | 436/40 |
| 3,355,367 | 11/1967 | Marsh | 436/40 X |
| 3,753,656 | 8/1973 | Matson et al. | 436/39 |
| 4,696,904 | 9/1987 | Stevens et al. | 436/39 |

OTHER PUBLICATIONS

Stevens et al., Anal. Chem., 59, 1716–1720, (1987).
Thompson et al., Anal. Chem., 42, 1474–1477, (1970).

Primary Examiner—Robert J. Warden
Assistant Examiner—Jeffrey R. Snay
Attorney, Agent, or Firm—Zarley, McKee, Thomte, Voorhees & Sease

[57] ABSTRACT

A sensitive method for the determination of water in the presence of common interferences is presented. The detection system is based on the effect of water on the equilibrium which results from the reaction aryl aldehydes, such as cinnamaldehyde and methanol in the eluent to form cinnamaldehyde dimethylacetal, plus water. This equilibrium is shifted in a catalytic atmosphere of a hydrogen ion form past column reactor. The extent of the shift and the resulting change in absorbance are proportional to the amount of water present.

17 Claims, 1 Drawing Sheet

LIQUID CHROMATOGRAPHIC DETERMINATION OF WATER

GRANT REFERENCE

This invention was made with Government support under Contract No. W-7405-ENG-82 awarded by the Department of Energy. The Government has certain rights in the invention.

BACKGROUND OF THE INVENTION

The quantitative determination of water in organic and inorganic materials is a frequently encountered important problem in analytical chemistry. The Karl Fischer method has long been the most widely used method for water determination. The Karl Fischer method involves a reagent which is usually composed of a solution of iodine, sulfur dioxide, and pyridine in methanol. In carrying out the Karl Fischer determination of water, the sample to be examined is preferably dissolved in methanol and then titrated with the above mentioned solution. The Karl Fischer method requires some considerable skill to carry out and cannot be used for samples that contain oxidizing or reducing substances or certain other chemicals. Some of the limitations of use of Karl Fischer reagents in aquametry are described in Stevens, U.S. Pat. No. 4,696,904 issued Sept. 29, 1987, which relates to an electrochemical detection system for indirect determinations of water. However, that process, too, has its deficiencies.

As can be seen there is, therefore, a continuing need for the development of a water detection system capable of widespread use for both organic and inorganic chemicals, which accurately detects the presence of water in a quantitative fashion. This invention has as its primary objective the fulfilling of the above referred-to need.

Another objective of the present invention is to provide a liquid chromatographic technique which involves a reaction between an aryl aldehyde and methanol that shifts its chemical balance depending upon the presence of water, and to detect and determine the presence of water indirectly by detecting and determining the amount of aryl aldehyde present.

Another objective of the present invention is to provide a detection system for use in aquametry which is economical, reliable, speedy, accurate, and versatile in the sense that it can be used for both organic and inorganic quantitative analysis.

The method and manner of accomplishing each of the above objectives will become apparent from the detailed description which follows hereinafter.

SUMMARY OF THE INVENTION

Figure 1:
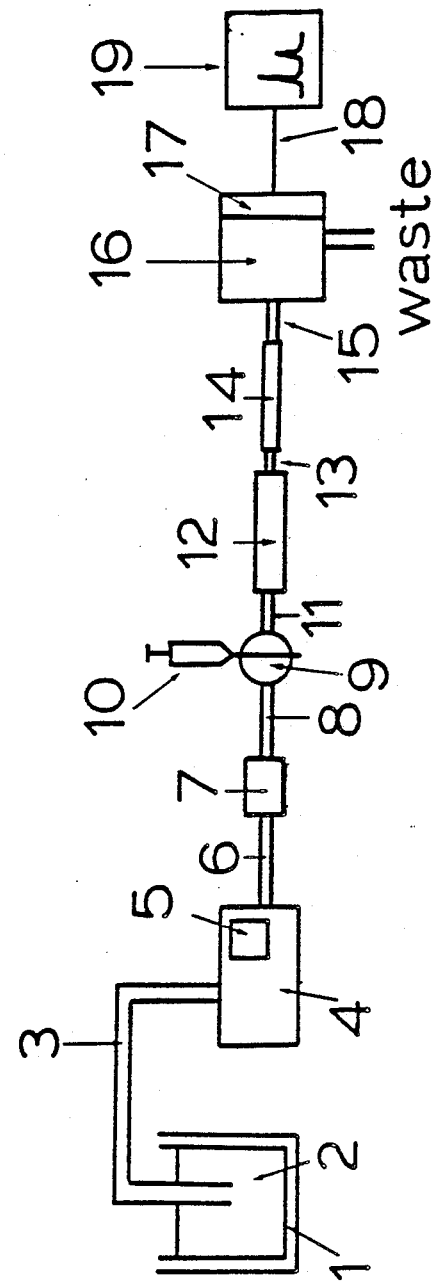
FIG. 1 is a schematic illustration of a typical apparatus which may be used for implementing the detection system of this invention.

A method for quantitative determination of water by liquid chromatography. The method involves adding to a flowing stream of methanol-based eluent a small but water detecting effective amount of an aryl aldehyde; introducing a chemical sample plug for testing into the eluent stream; eluting the eluent stream sample plug mixture through a separating medium to separate any water component from the balance of said stream; passing the emerging stream through a hydrogen-ion exchange resin column wherein the aryl aldehyde and methanol react to provide an acetal and water. This reaction is capable of equilibrium shifting depending on the presence of water, and thus spectrophotometrically detecting the amount of aryl aldehyde, and comparing it with a known background determination for aryl aldehyde for the system prior to introducing the chemical sample plug allows deter-mining the amount of water present in the chemical sample plug.

DETAILED DESCRIPTION OF THE INVENTION

The instrumentation used for the detection system of the present invention is known and is briefly schematically illustrated in FIG. 1. There, eluent reservoir 1 containing eluent 2 is fed to pump 4 through line 3. Pressure gauge 5 indicates eluent pressure in the portion of the system prior to the column 12. Eluent is pumped through line 6 pulse dampener 7, and line 8. Injection valve 9 is used to intro-duce the sample into the system. Sample is loaded into the injection valve 9 by a syringe 10. Sample and eluent pass through line 11 to the separator column 12, through line 13 to the catalyst column 14, and through line 15 to the detector flow cell 16, then out to waste. The detector electronics 17 relay the signal for the water peak to a recorder 19 through electrical connection 18.

The details of the precise instruments used for the example experiments are given hereinafter. It should however be understood that other instruments are readily available which may be systematically arranged to accomplish the process of the present invention. Put another way, the invention is the method, not the precise quantitative instruments used to accomplish the method.

This invention uses a flowing stream of methanol-based eluent which contains a small but water detecting effective amount of an aryl aldehyde to provide a methanol based eluent mixture. The column eluent is here described as a "methanol-based" eluent, and it is critical to the invention that it be "methanol-based." It does not, however, have to be pure methanol. It can, for example, be methanol mixed with, for example, acetonitrile on a 60:40 weight basis of acetonitrile to methanol. Acetonitrile is mentioned by way of example only as one of the additives which is a helpful enhancer for the liquid chromatography detection mentioned hereinafter. Other eluent enhancers may be mixed with the methanol to accomplish the same purpose and include carbon tetrachloride, chloroform, cyclohexane, heptane, tetrahydrofuran and toluene. The important feature is that they must be water-free. The ratio of eluent chromatographic detection enhancer to the methanol can be within the range of from 40 parts enhancer up to 60 parts enhancer, but is preferably about 50:50.

The aryl aldehyde added to the methanol-based eluent can, for example, be benzaldehyde, but is preferably an aryl alkenyl aldehyde, wherein the alkenyl is from $C_2$ to $C_{10}$. The term aryl aldehyde as used herein is intended to include aryl aklenyl aldehydes. Most preferably the aldehyde is cinnamaldehyde which reacts with methanol to form a dimethylacetal, plus water. The amount of aryl aldehyde is not critical and can vary from 0.1 mM to 10 mM, but is preferably within the range of from about 0.15 mM to 5 mM.

After the methanol-based eluent aryl aldehyde mixture is prepared, it is then run through the detection system to provide a background comparison detection spectrogram for the quantity of aryl aldehyde present in the eluent. As explained hereinafter, this background detection spectrogram number is used for determining the amount of water present.

In the next step of the process of this invention, a chemical sample to be tested, referred to in the art as a chemical sample plug, is added to the eluent stream mixture to provide a flowing stream of eluent mixture and the chemical sample plug. The chemical nature of the sample plug is almost limitless in this invention and can include either any inorganic matrix or any organic matrix in which the water quantity is to be tested. Indeed, it is one of the advantages of the present invention that it has widespread versatility for water determinations of both organic and inorganic samples. For example, the results can be determined for toluene, ethyl acetate, acetone, 3-mercaptopropionic acid, ascorbic acid, and for inorganic salts to determine if they have present water of hydration such as, for example, copper(II) chloride dihydrate. In short, the precise chemical sample plug for testing is not critical and it is one of the objectives of the present invention that it is not limiting and that it can be a wide variety of either organic or inorganic chemicals.

The amount of chemical sample plug added to the stream need not be large and is not critical, but generally may vary over a range of from 0.001 molar to 0.5 molar, and preferably from 0.01 molar to 0.1 molar, and most preferably about 0.05 molar. The chemical sample plug is injected through injection valve 10 into the flowing stream of eluent mixture.

In the next step the mixture of methanol-based eluent to which is added the aryl aldehyde and now the chemical sample plug, is passed through a separating medium to separate any water component present in the chemical sample plug from the balance of the eluent stream so that the separated water component emerges from the separating medium at a different time than the chemical sample plug.

A typical cation exchange columns can be used for this water separation technique and such are well-known. Those suitable as cation exchange resins are those that have a known affinity for water, see for example *DOWEX:: Ion Exchange,* published by The Dow Chemical Company, 1964, specifically page 33, and Roof, supra. Another separating medium is a chromatographic column of sulfonated styrene-divinyl-benzene copolymer/acid-type ion-exchange resin such as Bio-Rad Laboratories (P.O. Box 4031, Richmond, California 94804) Aminex®, 50WX4, 20 to 30 micron size, catalog number 147-4203, packed in a Cheminert® Model L9-9MA-13 column available from The Anspec Company, P.O. Box 7730, Ann Arbor, Michigan 48107, catalog number H7224. Other ion-exchange mediums such as quaternized styrene-divinylbenzene copolymer base-type ion-exchange resins such as Bio-Rad Laboratories, supra. AG® 1 X 2, 200 to 400 mesh size, catalog number 745-1241. Also useful in the invention are silica based ion-exchange columns such as Whatman Corporation's Partisil® SAX anion exchange column or Partisil SCX cation exchange column, available from The Anspec Company, supra, catalog number H6303 and H6311, respectively. For the present invention, the preferred cation exchange resin is a cation exchange column in the Li+ form for the chromato-graphic separation of water. One preferred column that has been used successfully is Aminex Q-150S in the lithium form.

The precise separating medium column employed is not critical, but what is critical is that it effectively chromatographically separates the water component of an injected chemical sample plug from the other components of the sample when using a non-aqueous eluent.

In the next step of this invention, the emerging stream of chemical sample plug is passed through a hydrogen ion exchange resin column wherein the aryl aldehyde and the methanol react to provide a corresponding acetal and water in a reaction which is capable of equilibrium shifting, depending on the presence of water. Using as an example the preferred aryl aldehyde, cinnamaldehyde, the detection of water is based on a chemical reaction which occurs when water and an acetal are present together with an acid catalyst. When the eluent passes through the catalyst column, the following reaction occurs between the trans-cinnamaldehyde and the methanol:

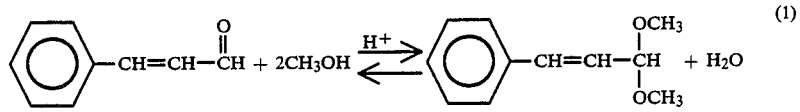
(1)

Although the cinnamaldehyde absorbs ultraviolet light at 310 nm, the acetal formed upon passage through the column in the H+ form does not. Consequently, the background absorbance is very low.

When water is present in an injected chemical sample plug, the water forces the above equilibrium in the reverse direction, reforming the cinnamaldehyde:

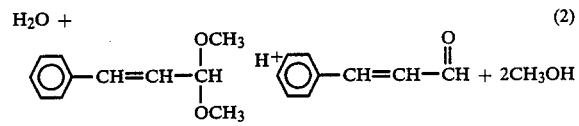
(2)

With the detector wavelength (herein described) set at 310 nm, an increase in absorbance is seen as water elutes. This absorbance change is proportional to the amount of water in the sample injected. Consequently, linear calibration plots of absorbance versus percent of water in the sample can be obtained.

The cinnamaldehyde absorbs strongly at a detector wavelength of 310 nm, while the acetal of cinnamaldehyde has little absorbance at this wavelength, as evidenced by the fact that a solution of cinnamaldehyde in methanol is allowed to stand for up to two days, the absorbance at 310 nm remains unchanged. Thus, using cinnamaldehyde as the example of the aryl aldehyde, the wavelength of 310 nm should be used for maximum sensitivity and the optimum signal to noise ratio, with the background being quite low. In short, the extent of the shift in the equilibrium in reaction (2) measured by the increased absorbance at 310 nm is proportional to the amount of water in the sample. Similar background determinations for other aryl aldehydes can be determined and used if they are used in conjunction with the methanol-based eluent in lieu of the preferred cinnamaldehyde.

It is preferred that the aryl aldehyde be an alkenyl aldehyde because the use of side chain branching which has some unsaturation enhances the ultraviolet light absorbance in the spectrophotometric detection. It is, however, possible that aryl aldehydes without unsaturation such as benzaldehyde can be used. Indeed, testing confirms that benzaldehyde does work but that the detection is easier if there is unsaturation present. Therefore the aryl alkenyl aldehydes are preferred.

The precise ultraviolet light spectrophotometer used is not critical. This method is so powerful for the determination of water because it combines a selective detection method with the selectivity of chromatography. Because the reaction used for detection occurs after the separation of the water component, water can be determined in the presence of substances which would interfere if the separation column were not employed, i.e., aldehydes and ketones, which react with methanol in the presence of an acid catalyst to form water. This was tested by determining water in acetone. Acetone would be expected to react with methanol to form water (plus a ketal) when it entered a catalytic column. However, it is already separated chromatographically from the water in the sample before it reaches the catalytic second column and no interference is encountered.

This same reasoning holds for sample components that absorb at the detection wavelength. They do not interfere with the quantitative determination of water as long as they are separated chromatographically before entering the catalytic detection system. Cinnamaldehyde works better than many aldehydes in the detection system because the wavelength of 310 nm is above the UV-cutoff for many organic solvents.

The response factor (RF) of the chromatographic detection system for water was measured in the following units:

$$RF = \frac{\text{signal in } Au \text{ at 310 nm}}{0.1\% \text{ water in sample}}$$

Response factors of 0.012 and 0.071 were obtained for a long column with a 20-microliter sample loop and a short column with a 100-microliter sample loop, respectively. These are quite good, considering that the baseline noise with this system was approximately $2 \times 10^{-5}$ AU.

The limit of detection for water will depend on the response factor, the size of sample loop used and on the amount of water in the eluent. The water content of the eluent can be estimated by extrapolating a linear plot of peak height versus ppm water in standards to zero peak height. The most critical factor in obtaining extremely low detection limits for water seems to be to prepare and use an eluent of exceptionally low water content.

The following examples are offered to further illustrate but not limit the process and system of the present invention.

EXAMPLES

The utility of this method was demonstrated by separating and determining water on a long column in each of the following samples: toluene, ethyl acetate, acetone, 3-mercaptopropionic acid, ascorbic acid (dissolved in methanol), and copper(II) chloride dihydrate (dissolved in methanol). Samples analyzed for water on the short column included isopropyl alcohol, toluene, ethylacetate, and "absolute" ethanol. Analysis of the mercaptan, ascorbic acid and copper(II) chloride samples by the Karl Fischer method used for comparison purposes here was not possible. Likewise, aldehydes and ketones interfere in a liquid chromatographic method that uses a different detection system other than the present one.

Results are shown in Table I and II. The results in Table I, for toluene, ethyl acetate and acetone, were checked by comparison with the Karl Fischer method. The ethyl acetate sample was further checked by spiking it with 0.100% water. Recovery was excellent. Table II shows results for those samples for which a Karl Fischer titration would have yielded erroneous results. These samples were checked by analyzing a blank, then spiking the sample and reanalyzing. In the case of the 3-mercaptopropionic acid, due to the small amount of mercaptan available, a 10.00% solution of the mercaptan in methanol was spiked. Recoveries were again very good.

TABLE I

Liquid chromatographic determination of water in organic solvents.

| sample | % water added | % water found (this method) | % water found (Karl Fischer) |
|---|---|---|---|
| neat toluene | 0 | 0.0253 | 0.0251 |
| neat acetone | 0 | 0.321 | 0.325 |
| neat ethyl acetate | 0 | 0.0950 | — |
| ethyl acetate spiked with 0.100% water | 0.100 | 0.196 | 0.198 |

TABLE II

Liquid chromatographic determination of water in the presence of common interferences.

| sample | % water added | % water calculated (spike plus blank) | % water found |
|---|---|---|---|
| neat 3-mercaptopropionic acid | 0 | N.A. | 0.494 |
| methanolic solution of 10.00% 3-mercaptopropionic acid, spiked with 0.200% water | 0.200 | 0.249 | 0.246 |
| methanolic solution of 0.057M ascorbic acid | 0 | N.A. | 0.0080 |
| methanolic solution of 0.057M ascorbic acid spiked with 0.100% water | 0.100 | 0.108 | 0.104 | the apparatus, the eluent and sample solutions, and the titration solutions used for the Karl Fischer reagent, as well as the chromatographic conditions employed in these examples for Tables I and II are set forth below.

Apparatus. The instrument used consisted of a model 302 Gilson single piston pump, a model 7125 Rheodyne injector equipped with either a 20-microliter or a 100-microliter sample loop, a model LP-21 Scientific Systems, Inc. Lo-Pulse pulse-dampener, either a glass 8 mm × 10 cm or a stainless steel 4.6 mm × 5 cm column packed with Bio-Rad Aminex Q-150S in the $Li^+$ form (separation column), a 2 mm × 10 cm stainless steel column packed with Bio-Rad Aminex Q-150S in the $H^+$ form (catalyst column), a Spectroflow 783 Kratos absorbance detector, and a Curken strip-chart recorder. The columns were packed using upward slurry packing. However, a balanced density method was not used. Due to the large degree of shrinking and swelling that occurs in polystyrene-divinyl-benzene resins when a change in solvent occurs, it was necessary to pack the column in the solvent used in the mobile phase.

Eluent and Sample Solutions. Trans-cinnamaldehyde, 99% (Aldrich Chemical Co.), was used without purification. Reagent grade methanol (Mallinckrodt) and HPLC grade acetonitrile (Fischer Scientific) were dried by storing over activated 3 angstrom molecular sieves (Aldrich) for at least a week. The 3-mercaptopropionic acid (Aldrich) was 99+% pure. All other samples were reagent grade and used without purification.

For maximum sensitivity and reproducibility, the eluent and all samples were prepared in a nitrogen-filled glove bag. Once prepared, the eluent was protected from atmospheric moisture by bubbling nitrogen through the solution and out through a drying tube filled with anhydrous calcium sulfate (Drierite). All sample solutions were placed in vials equipped with Miniert valves (Supelco) prior to removal from the glove bag. The valve and septum of the Mininert caps allowed removal of an aliquot without exposing the remainder of the sample to atmospheric moisture.

Titrations. Karl Fischer Reagent (titer 2.8 mg/mL) was purchased from Aldrich and standardized. The burette was flushed with nitrogen prior to being filled and then blanketed with nitrogen during the titration. A large (50 mL) burette was used so that a standard and three samples could be titrated without refilling the burette. Samples were titrated in volumetric flasks blanketed with nitrogen to minimize exposure to atmospheric moisture. A visual endpoint was used.

Chromatographic Conditions. All chromatography was done at a flow rate of either 1 mL/min (the long separation column) or 0.8 mL/min (the short separation column). A detector wavelength of 310 nm was used. The eluent was 0.794 mM transcinnamaldehyde in 60/40 acetonitrile/methanol.

Column Length. Many of the separations were done on a fairly long column (10 cm $\times$ 8 mm with a 10 cm $\times$ 2 mm catalyst column) in order to obtain good resolution of the water peak in some difficult samples.

In many cases a shorter column can be used and the chromatographic separation of water greatly speeded up. Using a short column (5 cm $\times$ 4.6 mm with a 10 cm $\times$ 2 mm catalyst column) good separations were obtained for 367 ppm water in isopropyl alcohol and for 184 ppm water in toluene.

One Column Method. While this example describes two columns, only one column may be used, filled with Aminex Q-150S in the $H^+$-form. Water entering the separation column is converted to cinnamaldehyde in the first part of the column by shifting the equilibrium in equation 2 towards the right. The species actually separated on the column is the cinnamaldehyde produced. This was confirmed by using an eluent of only methanol and injecting cinnamaldehyde. Two peaks were obtained, one large peak eluting very early in the chromatogram, and one small peak eluting at the retention time seen for water when cinnamaldehyde was in the eluent. The detector wavelength was varied and peak heights versus wavelength were plotted. Since the plots for the early and late peaks matched the UV spectra of the acetal and cinnamaldehyde, respectively, it was concluded the early peak was the acetal and the peak with the same retention time as water was cinnamaldehyde.

With the one-column method, aldehydes and ketones are substantially retained; all those tested have approximately the same retention time as cinnamaldehyde and therefore interfere with the determination of water. However, most organic solvents are not retained by the column and consequently pose no problem. Interference from aldehydes and ketones, and possibly from other types of sample material, can be avoided by using cation-exchange column in the $Li^+$-form for the chromatographic separation of water, followed by a short cation-exchange column in the $H^+$-form to catalyze the reaction needed for detection, as earlier described.

One final application of this method is that it may be used for the determination of water of hydration in inorganic salts. A sample of $CuCl_2H_2O$ was analyzed and found to contain 1.99 moles $H_2O$ per mole of $CuCl_2$. This determination could not be done with a Karl Fischer titration since the $Cu(II)$ would be reduced to $Cu(I)$ by the reagent.

Of all organic samples tested, only dimethyl sulfoxide was found to interfere because it produced a very large peak that obscured the water peak. Of the inorganic samples tested, metal hydroxides interfered. Since the columns involved are ion exchange columns, any cation injected will cause the release of a corresponding amount of hydrogen ion. In the case of metal hydroxides, this hydrogen ion will react with the hydroxyl to form water giving erroneously high results. Other than these limitations, however, the process seems to have wide applicability.

It can be seen that in comparison with the traditional standard of the Karl Fischer method, the present invention has wider applicability and has equally sensitive valid results.

What is claimed is:

1. A method for quantitative determination of water by liquid chromatography comprising the steps of:
   (a) adding to a flowing stream of methanol-based eluent a water detecting effective amount of an aryl aldehyde to provide a methanol-based eluent mixture;
   (b) introducing a chemical sample plug to be tested into the eluent mixture to provide a flowing stream of eluent stream chemical sample plug mixture;
   (c) eluting the eluent stream sample plug mixture through a separating medium effective to separate any water component present from said eluent stream sample plug mixture so that the separated water component emerges in an emergency stream from the separating medium at a different time than the chemical sample plug; and
   (d) passing the emerging stream through a hydrogen ion exchange resin column wherein said aryl aldehyde and said methanol react to provide an acetal and water in a reaction which is capable of equilibrium shifting in the presence of water; and thereafter,
   (e) spectrophotometrically detecting the amount of aryl aldehyde in a stream emerging from said column by measuring a characteristic ultraviolet light absorbance thereof, and
   (f) correlating said detected amount of aryl aldehyde to an amount of water present in said chemical sample plug.

2. The method of claim 1 wherein said separating medium effective to separate a water component from the balance of said eluent stream sample plug mixture is a cation exchange resin.

3. The method of claim 2 wherein said cation exchange resin is a cation exchange resin in the lithium form.

4. The method of claim 1 wherein the amount of aryl aldehyde is from 0.1 micromoles to 10 micromoles.

5. The method of claim 4 wherein the amount of aryl aldehyde is from about 0.15 micromoles to about 5 micromoles.

6. The method of claim 1 wherein the methanol-based eluent is methanol.

7. The method of claim 6 wherein the methanol-based eluent is a combination of methanol and a non-aqueous UV spectrogram enhancer.

8. The method of claim 7 wherein the enhancer is acetonitrile.

9. The method of claim 1 wherein said aryl aldehyde is an aryl alkenyl aldehyde.

10. The method of claim 9 wherein said alkenyl moiety is from $C_2$ to $C_{10}$ in carbon length.

11. The method of claim 6 wherein said aryl alkenyl aldehyde is cinnamaldehyde.

12. The method of claim 1 wherein said chemical sample plug is an organic chemical sample plug.

13. The method of claim 12 wherein the concentration of chemical sample plug in the eluent mixture is from about 0.001 molar to about 0.5 molar.

14. The method of claim 13 wherein the concentration of chemical sample plug in the eluent mixture is from about 0.01 molar to about 0.1 molar.

15. The method of claim 1 wherein said chemical sample plug is an inorganic chemical sample plug.

16. The method of claim 15 wherein the concentration of chemical sample plug in the eluent mixture is from about 0.001 molar to about 0.5 molar.

17. The method of claim 16 wherein the concentration of chemical sample plug in the eluent mixture is from about 0.01 molar to about 0.1 molar.

* * * * *